United States Patent

Kreuzer

[11] 4,044,257
[45] Aug. 23, 1977

[54] RETENTION TIME CHROMATOGRAPH EMPLOYING AN IR ABSORPTION SPECTROGRAPHIC DETECTOR

[75] Inventor: Lloyd B. Kreuzer, San Francisco, Calif.

[73] Assignee: Diax Corporation, Palo Alto, Calif.

[21] Appl. No.: 551,379

[22] Filed: Feb. 20, 1975

[51] Int. Cl.² .................................................. G01J 1/00
[52] U.S. Cl. ...................................... 250/344; 250/343
[58] Field of Search .................. 250/343, 344; 73/23.1; 55/197; 356/97

[56] References Cited

U.S. PATENT DOCUMENTS

| | | | |
|---|---|---|---|
| 3,279,308 | 10/1966 | Bartz et al. | 250/343 |
| 3,638,396 | 2/1972 | Lovelock | 55/197 |
| 3,700,890 | 10/1972 | Kreuzer | 250/343 |
| 3,727,050 | 4/1973 | Kerr | 250/343 |
| 3,728,540 | 4/1973 | Todd et al. | 250/343 |
| 3,766,380 | 10/1973 | Menzies | 250/343 |
| 3,820,901 | 6/1974 | Kreuzer | 356/97 |
| 3,860,393 | 1/1975 | Campen | 73/23.1 |
| 3,896,312 | 7/1965 | Brown et al. | 250/343 |
| 3,902,068 | 8/1975 | Wood | 250/343 |

Primary Examiner—Alfred S. Smith
Assistant Examiner—B. C. Anderson
Attorney, Agent, or Firm—Harry E. Aine

[57] ABSTRACT

Sample material of retention time peaks of a chromatograph are exposed to infrared radiation at first and second wavelengths and the absorption of the infrared energy by the sample peak is measured. The measured infrared absorption at the first and second wavelengths is correlated with the retention time of the sample peak as an identification of the sample material. In addition, overlapping retention time peaks are resolved by detecting the change in the ratio of the infrared absorption at the first and second wavelengths as a function of retention time for a given peak.

14 Claims, 1 Drawing Figure

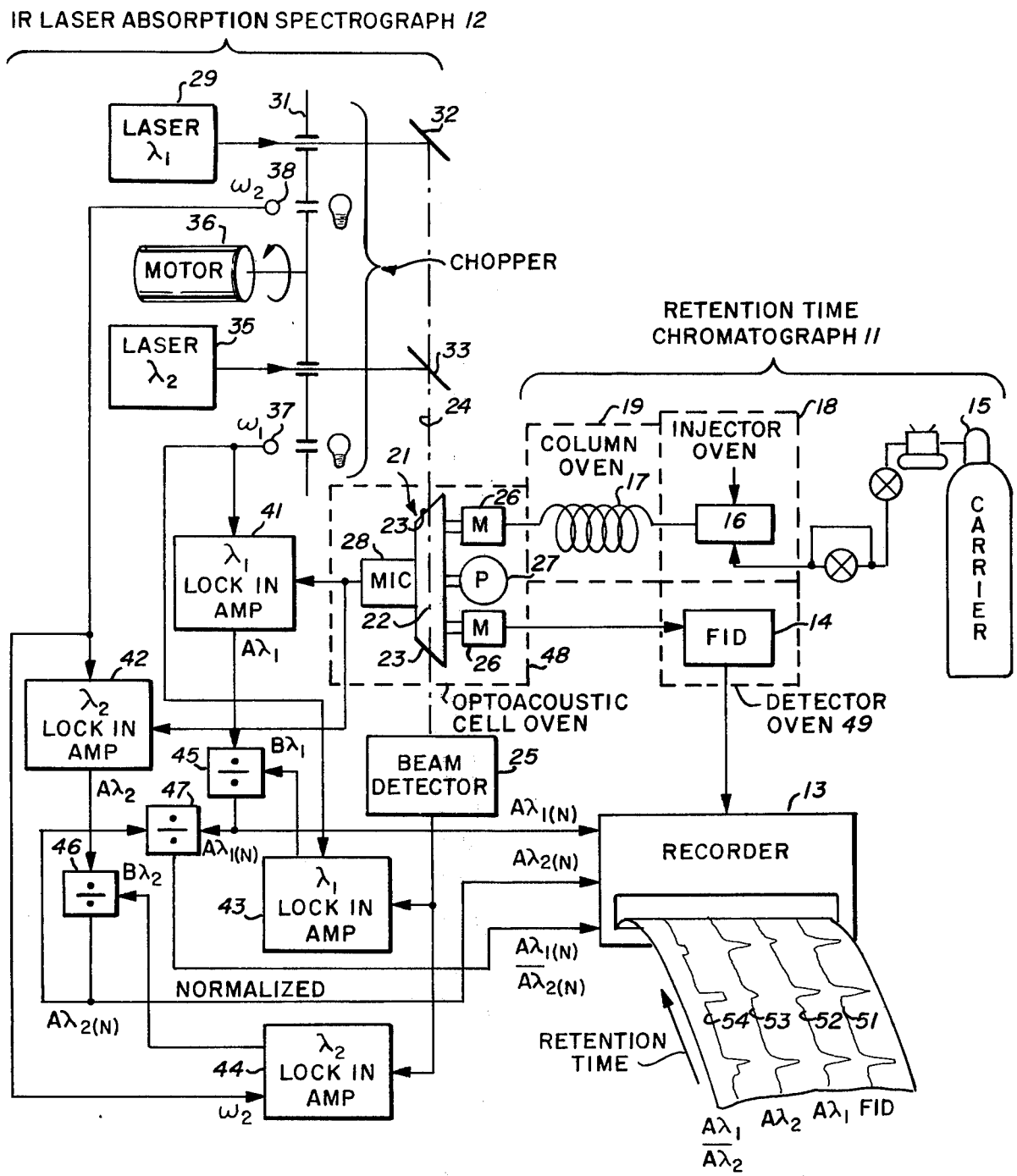

RETENTION TIME CHROMATOGRAPH EMPLOYING AN IR ABSORPTION SPECTROGRAPHIC DETECTOR

BACKGROUND OF THE INVENTION

The present invention relates in general to retention time chromatography and, more particularly, to an improved detection scheme for use with a retention time chromatograph for identifying and/or resolving sample constituents of a retention time peak or peaks.

DESCRIPTION OF THE PRIOR ART

Heretofore, it has been proposed to employ an infrared laser absorption spectrographic detector in combination with a retention time chromatograph for identifying and/or resolving materials in the effluent stream of the retention time chromatograph. Such proposals have been made in *Analytical Chemistry*, Vol. 44, No. 4 of Apr. 1973 and in *Analytical Chemistry*, Vol. 46, No. 2 of February 1974 pages 239-244. In these proposed schemes, it was contemplated that laser absorption measurements at a number of wavelengths would be obtained for the effluent stream of a retention time chromatograph for identifying and/or resolving various constituents of the effluent stream. Each different sample constituent would have a different infrared absorption spectrum. By obtaining the infrared absorption spectrographic data and comparing this data with spectrographic data of pure compounds stored in a memory the various sample constituents would be resolved and/or identified.

More particularly, a method for resolving and/or identifying sample constituents by obtaining an infrared spectrum of the sample under analysis is disclosed in an article titled "Air Pollution: Sensitive Detection of Ten Pollutant Gases by Carbon Monoxide and Carbon Dioxide Lasers" appearing in *Science*, Vol. 177, pages 347-349 of July 28, 1972 and in U.S. Pat. No. 3,820,901. However, these schemes, wherein the infrared laser absorption spectrum is compared at a number of points for resolving the various constituents, is relatively time consuming and it would be desirable to provide a detection scheme which would be faster and which would be capable of real time analysis of a retention time peak of a chromatograph.

It is also known to identify retention time peaks by feeding a sample of the effluent stream of a retention time chromatograph through a suitable gas handling system into a mass spectrometer. In this case, the mass spectrometer is used as a gas chromatograph detector to identify peaks by their mass spectra. These systems are currently complex and expensive and often produce more data than required. For example, one way to identify a retention time peak is to look at a four mass point spectrum of the peak. This is then used to search a data file for possible compounds. Quite often, in the case of relatively complex molecules the mass spectrometer fragments the molecule into a number of fragments which may be common to many different types of molecules. Thus, the data analysis can be relatively complex and expensive. Thus, there is a need for a method for identifying retention time peaks which is preferably nondestructive of the sample material and which, in addition, is less expensive to manufacture and less time consuming.

SUMMARY OF THE PRESENT INVENTION

The principal object of the present invention is the provision of an improved method and apparatus for identifying retention time chromatograph peaks and, more particularly, to such a system which may be employed to resolve overlapping retention time peaks on a real time basis.

In one feature of the present invention, a retention time peak of a chromatograph is identified by correlating the retention time of the sample peak with detected infrared absorption outputs derived at first and second infrared wavelengths, whereby the constituent of the retention time peak is identified.

In another feature of the present invention, the ratio of the absorption of a sample material of a retention time peak at different infrared wavelengths is correlated with the retention time to resolve overlapping retention time peaks.

In another feature of the present invention, the ratio of the absorption of infrared radiation at two different wavelengths by the sample constituents of a retention time peak is monitored as a function of time for detecting any time dependent changes in the ratio of the measured absorption for resolving overlapping retention time peaks.

Other features and advantages of the present invention will become apparent upon a perusal of the following specification taken in connection with the accompanying drawings wherein:

BRIEF DESCRIPTION OF THE DRAWINGS

The drawing is a schematic diagram, partly in block diagram form, of a retention time chromatograph and laser absorption spectrographic detector system incorporating features of the present invention.

DESCRIPTION OF THE PREFERRED EMBODIMENTS

Referring now to the drawing, there is shown a retention time chromatograph 11 employing an infrared laser absorption spectrographic detector 12 of the present invention. The retention time chromatograph 11 has its fluid effluent output stream fed through a laser optoacoustic spectrographic detector 12 to derive outputs which are fed to a recorder 13 for recording the retention time chromatograms of sample material analyzed by the retention time chromatograph 11. In addition, the effluent stream emerging from the infrared laser absorption spectrograph 12 is fed through a conventional flame ionization detector 14 for otaining the conventional retention time chromatographic information which is fed to the recorder 13 for recording as a function of the chromatograms derived from the infrared laser absorption spectrograph 12.

More particularly, the retention time chromatograph 11 includes a source 15 of carrier gas such as helium which is fed via suitable regulators and valves to the input of a sample injector 16 which serves to inject sample material to be analyzed into the input carrier gas stream which is thence fed into the chromatographic column 17. The column 17 separates the various constituents of the sample material in the fluid stream in accordance with their respective retention times for a specific packing material of the column 17 and the particular temperature of the column. Both the injector 16 and the column 17 are contained within their ovens 18 and 19, respectively, for controlling the temperatures of the injector and column, as desired.

The output effluent stream of the column 17 is thence fed through an optoacoustic detector cell 21 of the infrared laser absorption spectrograph 12. The optoacoustic detection cell 21 includes a chamber 22 having Brewster angle windows 23 on opposite sides thereof in axial alignment with an infrared laser beam path 24 passable through the detection cell 21 to a beam detector 25 which detects the beam power. A pair of mufflers 26 are connected to the input and output fluid flow passageways leading to and from of the detector cell 21 for decoupling the interior chamber 22 of the detection cell 21 from acoustic noise sources external of detector cell 21, such as those tending to propagate through the fluid stream into the detector 21. A pressure regulator 27 is also coupled in fluid exchanging relation with the detection cell chamber 22 for maintaining a predetermined constant fluid pressure therein. A microphone 28 is coupled in acoustic wave energy exchanging relation with the sample volume within the chamber 22 for detection of absorption signals generated by absorption of energy from the laser beam by the sample constituents.

A first infrared laser 29 which generates an output beam of coherent I.R. radiation at a first infrared wavelength $\lambda_1$ directs its beam through a chopper wheel 31 to a mirror 32 which directs the beam through a half-silvered mirror 33 into the beam path 24 passing through the detector cell 21 to the beam detector 25. Also, a second laser 35 produces a second infrared laser beam at $\lambda_2$ which is directed through a second ring of perforations in the chopper wheel 31 to the half-silvered mirror 33 and thence into the common beam path 24 through the detector cell 21 to the beam detector 25. The first and second sets of perforations in the chopper wheel 31, which is driven by a motor 36, serves to chop the respective beams of the two lasers 29 and 35 at different modulation frequencies, such as 25 Hertz and 55 Hertz, respectively. Modulation reference signals are derived at the two modulation frequencies $\omega_1$ and $\omega_2$ by directing light back through the perforations of the chopper wheel to optical detectors 37 and 38, respectively.

Absorption of a sample constituent in the effluent stream of the chromatograph 11 within the chamber 22 of the detector cell 21 produces absorption and heating of the sample volume at the modulation frequency of the laser beam wavelength being absorbed by that constituent. This modulated heating due to the absorption of the infrared energy by the sample constituent, produces an acoustic wave at the respective modulation frequency which is picked up by the microphone 28 and fed to the input of two lock-in amplifiers 41 and 42, respectively, for synchronous detection against respective samples of the modulation frequencies $\omega_1$ and $\omega_2$ to separate the absorption signals at the respective infrared wavelengths $\lambda_1$ and $\lambda_2$.

In a preferred embodiment of the present invention, the respective absorption signals $\Delta\lambda_1$ and $\Delta\lambda_2$ are normalized to the beam power at the respective wavelengths $\lambda_1$ and $\lambda_2$ by feeding the output of the beam detector 25 to lock-in amplifiers 43 and 44 for synchronous detection against samples of the modulation frequencies $\omega_1$ and $\omega_2$, respectively, to derive outputs $B\lambda_1$ and $B\lambda_2$ corresponding to the beam power at the respective wavelengths $\lambda_1$ and $\lambda_2$. These beam power signals are thence fed to the input of dividers 45 and 46 which serve to divide the respective absorption signals $\Delta\lambda_1$ and $\Delta\lambda_2$ by the respective beam power signals at $\lambda_1$ and $\lambda_2$ to derive normalized absorption output signals $A\lambda_{1\{n\}}$ and $A\lambda_{2\{n\}}$.

These normalized absorption signals are thence fed to the recorder 13 for recording as a function of time. In addition, the two normalized absorption signals are fed to the respective inputs of a divider 47 to derive the ratio $(A\lambda_{1\{n\}}/A\lambda_{2\{n\}})$ of the two absorption signals at $A\lambda_{1\{n\}}$ and $A\lambda_{2\{n\}}$ which is also fed to the recorder 13 for recording as a function of retention time.

The optoacoustic detection cell 21 is contained within an optoacoustic cell oven 48 for maintaining the temperature of the cell 21 at a constant predetermined temperature, as the infrared absorption is a function of sample temperature. The output effluent stream from the optoacoustic detection cell 21 is thence fed through a conventional chromatographic detector such as flame ionization detector 14 which is contained within its respective detector oven 49.

Thus, the recorder 13 records the conventional flame ionization detected retention chromatogram at 51 on the same time scale with the normalized absorption signal at $A\lambda_{1(n)}$ at 52, the normalized absorption signal at $\lambda_2$ namely $A\lambda_{2(n)}$ at 53 and the ratio of the absorption signals at $\lambda_1$ and $\lambda_2$ namely $(A\lambda_{1(N)}/A\lambda_{2(n)})$ at 54.

If the path length through the optoacoustic detention cell 21 is short enough and if the sample concentration is low enough so that the laser beam is not appreciably attenuated in passing through the chamber 22, i.e. less than one-percent attenuation, then the ratio of microphone signal at $\omega_1$ to the detected infrared beam power signal at $\omega_1$, namely, the normalized absorption signal $A\lambda_{1(n)}$ is proportional to the absorbing gas concentration and absorption strength at $\lambda_1$. The same holds for $\omega_2$ and $\lambda_2$. The condition of short optical path length and relatively weak absorption is $$kl < 0.01$$

where $k$ is absorbance and $l$ is the path length. For many gases $k \sim 10^{-5} C$ cm$^{-1}$ where C equals gas concentration in parts per million or nanograms per cc of carrier gas. Thus, for a typical example, $Cl < 10^3$.

Since sensitivity of an optoacoustic detector cell 21 is not increased by increasing $l$ it is desirable to keep $l$ short to get large dynamic range. A typical value for $l$ would be 1 centimeter. This means $C < 10^3$ (parts per million).

If C exceeds this value, the path length $l$ is preferably made shorter or a nonlinear nature of the absorption should be taken into account by using the logarithmic transformation of Beer's law. Assuming that the linearity, as above described holds, then the ratio R $$R = \frac{\text{microphone signal at } \omega_1}{\text{I.R. beam detector signal at } \omega_1}.$$

$$\frac{\text{I.R. beam detector signal at } \omega_2}{\text{microphone signal at } \omega_2}$$

is independent of sample concentration and depends only on sample composition.

The above ratio equals the ratio $(A\lambda_{1(n)}/A\lambda_{2(n)})$ measured as above described and recorded at 54. This quantity identifies sample or peak composition. If this quantity remains constant as the retention time peak passes through the flame ionization detector 14 it is a good indication that the respective retention peak is one pure compound. If a retention time peak represents two or more partially separated compounds, then the ratio $(A\lambda_{1(n)}/A\lambda_{2(n)})$ should change as the peak passes. This ratio quantity is readily measured to one-percent accuracy, even at low concentrations. Agreement of retention time and ratio $(A\lambda_{1(n)}/A\lambda_{2(n)})$ (to one-percent accuracy) provides a very accurate and reliable peak identification scheme. If this identification scheme was not sufficient to rule out other possible compounds, then other infrared wavelengths modulated or other modulation frequencies could be added to the system. Thus, a retention time peak would be characterized by retention time and one or more ratios of the absorption signals at different laser wavelengths.

As an alternative embodiment to using a plurality of infrared lasers 29 and 35, one or more tunable lasers 29 and 35 may be employed and they would be turned to obtain absorption at one or more wavelengths as the retention time peak passes through the sample detection cell 21.

Since infrared laser beams are narrow in wavelength spread, and infrared lasers, especially gas lasers, have very stable and reproducible emission wavelengths, these ratio measurements are truly characteristic of the compound and transferable with good accuracy from one system to another. The optoacoustic detection cell oven 48 and the pressure regulator 27 are preferably set to predetermined values since the infrared absorption signal depends on these quantities. Thus, the results are not directly transferable without error from one system to another except for situations wherein the same temperature and pressure exist for the detection cell 21 in the two systems.

What is claimed is:

1. In a method of identifying the sample material of a retention peak of a retention time chromatograph, the steps of:
   determining the retention time of a retention peak of a sample constituent in the effluent of a retention time chromatograph;
   detecting the absorption of infrared energy by the sample material of the retention peak from a laser beam at first and second infrared wavelengths of the laser beam;
   controlling the pressure of the sample constituent material to a predetermined value in a region wherein the absorption of the infrared energy from the laser beam is detected; and
   correlating the retention time of the sample peak with the detected absorption of the sample peak at said first and second infrared wavelengths to identify the sample constituent of the retention peak and deriving the ratio of the infrared absorption of the sample material of said retention peak at said first and second wavelengths; and
   wherein the step of correlating the retention time of the sample peak with the absorption of the sample at said first and second wavelengths comprises correlating said ratio with the retention time to identify the sample constituent.

2. The method of claim 1 including the step of, detecting time dependent changes in the correlation of the detected absorption of the sample peak at said first and second wavelengths as a function of retention time within a given peak to resolve overlapping retention peaks.

3. The method of claim 1 including the step of detecting changes in said ratio as a function of retention time within a given peak to resolve overlapping retention peaks.

4. The method for resolving constituents of a fluid sample including the steps of:
   deriving a pair of sample absorption signals which are a function of the absorption of infrared energy by constituents of the sample material from a laser beam of infrared radiation at first and second wavelengths $\lambda_1$ and $\lambda_2$, respectively;
   controlling the pressure of the fluid sample to a predetermined value in the region where the absorption signals are derived; and
   deriving an output proportional to the ratio of the two sample absorption signals at $\lambda_1$ and $\lambda_2$ said output being characteristic of the constituents in the fluid sample under analysis.

5. The method of claim 4 including the step of displaying at least one of the absorption signal outputs at $\lambda_1$ and $\lambda_2$.

6. The method of claim 4 including the step of deriving the ratio of the sample absorption signals as a function of time to detect time dependent changes in said ratio, such changes being indicative of changes in constituents of the sample under analysis.

7. The method of claim 6 wherein the fluid sample to be analyzed is the effluent stream of a retention time chromatograph and including the step of, correlating the derived ratio as a function of time with retention peaks of the retention time chromatograph for resolving overlapping chromatograph signal peaks.

8. Apparatus for identifying sample constituents of a retention peak of a retention time chromatograph including:
   means for determining the retention time of retention peak of a sample constituent in the effluent of a retention time chromatograph;
   means for detecting the infrared absorption of the sample material of the retention peak at first and second infrared wavelengths of coherent radiation;
   means for controlling the pressure of the sample material to a predetermined value in the infrared detection region where the absorption is detected; and
   means for correlating the retention time of the sample peak with the detected absorption of the sample peak at said first and second wavelengths to identify the sample constituent and means for deriving the ratio of the absorption of the sample material of said retention peak at said first and second wavelengths; and
   wherein said means for correlating the retention time of the sample peak with the absorption of the sample at said first and second wavelengths comprises means for correlating said ratio with the retention time to identify the sample constituent 9. The apparatus of claim 8 including, means for detecting time dependent changes in the correlation of the detected absorption of the sample peak at said first and second infrared wavelengths as a function of retention time within a given retention time peak to resolve overlapping retention peaks.

10. The apparatus of claim 8 including means for detecting changes in said ratio as a function of retention time within a given peak to resolve overlappig retention peaks.

11. In an apparatus for detecting constituents of a fluid sample employing the principle of absorption of infrared energy by the constituents in the fluid sample from an incident beam of infrared radiation:

means for deriving a pair of sample absorption signals which are a function of the absorption of infrared energy by constituents of the sample from an infrared laser beam of energy at first and second wavelengths $\lambda_1$ and $\lambda_2$, respectively;

means for controlling the pressure of the sample to a predetermined value in the region where the absorption of infrared energy by the sample is obtained; and means for deriving an output proportional to the ratio of the two sample absorption signals at $\lambda_1$ and $\lambda_2$ said output being characteristic of the constituents in the fluid sample under analysis.

12. The apparatus of claim 11 including means for displaying said ratio signal.

13. The apparatus of claim 11 including means for deriving said output proportional to the ratio of the sample absorption signals as a function of time to detect time dependent changes in said ratio which are indicative of changes in the constituents of the sample under analysis.

14. The apparatus of claim 13 including retention time chromatograph means having an effluent stream to be analyzed;

detector means for detecting the sample constituents as a function of retention time; and wherein said means for deriving the pair of sample absorption signals derives said signals from the effluent stream of the retention time chromatograph.

* * * * *